(12) United States Patent
Galley et al.

(10) Patent No.: US 7,812,047 B2
(45) Date of Patent: Oct. 12, 2010

(54) 4-IMIDAZOLINES

(75) Inventors: Guido Galley, Rheinfelden (DE);
Katrin Groebke Zbinden, Liestal (CH);
Roger Norcross, Olsberg (CH); Henri Stalder, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 26 days.

(21) Appl. No.: 12/146,497

(22) Filed: Jun. 26, 2008

(65) Prior Publication Data

US 2009/0012138 A1 Jan. 8, 2009

(30) Foreign Application Priority Data

Jul. 3, 2007 (EP) .................. 07111623

(51) Int. Cl.
*A61K 31/4174* (2006.01)
*C07D 233/12* (2006.01)
*C07D 233/16* (2006.01)

(52) U.S. Cl. .............. 514/399; 548/348.1; 548/351.1; 548/355.1

(58) Field of Classification Search .............. 548/300.1, 548/326.5, 348.1, 351.1, 355.1; 514/401, 514/399
See application file for complete search history.

(56) References Cited

U.S. PATENT DOCUMENTS

| | | | |
|---|---|---|---|
| 2,161,938 A | 6/1939 | Sonn | |
| 2,457,047 A | 12/1948 | Kyrides | |
| 2,731,471 A | 1/1956 | Synerholm et al. | |
| 2,744,909 A | 5/1956 | Speeter | |
| 2,744,910 A | 5/1956 | Speeter | |
| 2,778,836 A | 1/1957 | Morren | |
| 2,919,274 A | 12/1959 | Faust et al. | |
| 3,161,653 A | 12/1964 | Fruhstorfer et al. | |
| 3,354,175 A | 11/1967 | Fruhstorfer et al. | |
| 3,377,247 A | 4/1968 | Elbe | |
| 3,586,695 A | 6/1971 | Wysong et al. | |
| 3,622,579 A | 11/1971 | Stahle et al. | |
| 3,660,423 A | 5/1972 | Wysong et al. | |
| 3,758,476 A | 9/1973 | Rippel et al. | |
| 3,818,035 A | 6/1974 | Binon et al. | |
| 3,818,094 A | 6/1974 | Stahle et al. | |
| 3,992,403 A | 11/1976 | Roebke | |
| 4,125,620 A | 11/1978 | Stahle et al. | |
| 4,146,647 A | 3/1979 | Lafon | |
| 4,323,570 A | 4/1982 | Stenzel et al. | |
| 4,665,095 A | 5/1987 | Winn et al. | |
| 4,826,861 A * | 5/1989 | Gerard et al. .............. 514/371 |
| 5,610,174 A | 3/1997 | Craig et al. | |
| 5,658,938 A | 8/1997 | Geerts et al. | |
| 2002/0019390 A1 | 2/2002 | Wong et al. | |
| 2003/0181354 A1 | 9/2003 | Abdulrazik | |
| 2003/0236274 A1 | 12/2003 | Tasaka et al. | |

FOREIGN PATENT DOCUMENTS

| | | |
|---|---|---|
| CA | 2246027 | 2/2000 |
| EP | 0 024 829 | 3/1981 |
| EP | 0 125 410 | 11/1984 |
| EP | 0 166 937 | 1/1986 |
| EP | 0 331 374 | 9/1989 |
| EP | 0 424 059 | 4/1991 |
| EP | 0 857 483 | 8/1998 |
| EP | 0 924 209 | 6/1999 |

(Continued)

OTHER PUBLICATIONS

Defacqz, Nathalie et al, "Synthesis of C5-substituted imidazolines," Tetrahedron Letters (2003), vol. 44, pp. 9111-9114.*

(Continued)

*Primary Examiner*—Joseph K. McKane
*Assistant Examiner*—Janet L Coppins
(74) *Attorney, Agent, or Firm*—George W. Johnston; Patricia S. Rocha-Tramaloni; Kimberly J. Prior

(57) ABSTRACT

The present invention relates to compounds of formula

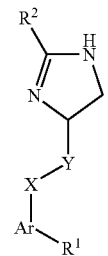

I wherein
$R^1$, $R^2$, X, Y and Ar are as defined herein
and to their pharmaceutically active salts, with the exclusion of the racemic compound 4-benzyl-4,5-dihydro-1H-imidazole or its tautomer (CAS 131548-83-9). Compounds of formula I have a good affinity to the trace amine associated receptors (TAARs), especially for TAAR1 and are useful for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

11 Claims, No Drawings

FOREIGN PATENT DOCUMENTS

| | | |
|---|---|---|
| EP | 1 103 243 | 5/2001 |
| EP | 1 413 576 | 4/2004 |
| ES | 323 985 | 12/1966 |
| FR | 6 551 | 12/1968 |
| GB | 877306 | 9/1961 |
| GB | 1016514 | 1/1966 |
| WO | WO 96/22768 | 8/1996 |
| WO | WO 97/12874 | 4/1997 |
| WO | WO 98/12183 | 3/1998 |
| WO | WO 01/30762 | 5/2001 |
| WO | WO 01/81334 | 11/2001 |
| WO | WO 02/22801 | 3/2002 |
| WO | WO 02/40453 | 5/2002 |
| WO | WO 02/076950 | 10/2002 |
| WO | WO 03/092374 | 11/2003 |
| WO | WO 2004/014898 | 2/2004 |
| WO | WO 2005/040166 | 5/2005 |
| WO | WO 2006/119411 | 11/2006 |
| WO | WO 2007/024944 | 3/2007 |
| WO | WO 2007/085556 | 8/2007 |
| WO | WO 2007/090720 | 8/2007 |

OTHER PUBLICATIONS

Deutch et al., (1999) Neurotransmitters. In Fundamental Neuroscience (2nd ed.) pp. 193-234, Academic Press.
Wong, et al., (2001) Nat. Rev. Neurosci. 2, pp. 343-351.
Carlsson. et al. (2001) Annu. Rev. Pharmacol. Toxicol. 41, pp. 237-260.
Tuite et al., (2003) Expert Opin. Investig. Drugs 12, pp. 1335-1352.
Castellanos et al., (2002) Nat. Rev. Neurosci. 3, pp. 617-628.
Usdin, E.; Sandler, M.; Editors. Psychopharmacology Series, vol. 1: Trace Amines and the Brain. [Proceedings of a Study Group at the 14th Annual Meeting of the American College of Neuropsychoparmacology, San Juan, Puerto Rico](1976), pp. 1-281.
Lindemann et al., (2005) Trends in Pharmacol. Sci. 26, pp. 274-281.
Branchek et al., (2003) Curr. Opin. Pharmacol. 3, pp. 90-97.
Premont et al. (2001) Proc. Natl. Acad. Sci. U. S. A. 98, pp. 9474-9475.
Mousseau et al., (1995) Prog. Brain Res. 106, pp. 285-291.
McCormack et al. (1986) J. Neurosci. 6, pp. 94-101.
Dyck, L. E. (1989) Life Sci. 44, pp. 1149-1156.
Parker, et al. (1988) J. Pharmacol. Exp. Ther. 245, pp. 199-210.
Lindemann et al. (2005) Genomics 85, pp. 372-385.
Flippin et al., Tetrahedron Letters, vol. 34, pp. 3255-3258 (1993).
Liebigs, Ann. Chem. pp. 2061-2071 (1980).
Huh et al., Tetrahedron, vol. 58, pp. 9925-9932 (2002).
Huh et al., Tetrahedron, vol. 60, pp. 9857-9862 (2004).
Law et al., J. Med. Chem. vol. 41, pp. 2243-2251 (1998).
Debernardis et al., J. Med. Chem. vol. 29, pp. 1413-1417 (1986).
Mohammadpoor-Baltork, Bull. Korean Chem. Soc. vol. 24, p. 1354-1356 (2003).
Abdollahi-Alibeik et al., Bioorg. Med. Chem. Lett. vol. 14, pp. 6079-6082 (2004).
Amemiya, Synth. Commun. vol. 20, pp. 2483-2489 (1990).
Ohta, Chem. Pharm. Bull. vol. 35, pp. 1058-1069 (1987).
Olah, Synlett pp. 647-650 (1992).
Katz et al., Tetrahedron, vol. 45, pp. 1801-1814 (1989).
Wentland et al., J. Med. Chem. vol. 30, pp. 1482-1489 (1987).
Campos et al., Heterocycles, vol. 40, p. 841-849 (1995).
Ohta, Synthesis, pp. 78-81 (1990).
Mancuso et al., J. Org. Chem. vol. 43, pp. 2480-2482 (1978).
Mohammadpoor-Baltork, Synlett, pp. 2803-2805 (2004).
Cahiez et al., Synthesis, pp. 2138-2144 (1999).
Evans et al., Tetrahedron Lett. vol. 39, pp. 2937-2940 (1998).
Nakamura et al., J. Chem. Soc. Perkin Trans. 1, pp. 1061-1066 (2002).
Turner, et al. (1991) J. Org. Chem. vol. 56, pp. 5739-5740.
Zhang et al., J. Med. Chem. 1997, 40, pp. 3014-3024.
Khimiya Geterotsiklicheskikh Soedinenii, 1988, pp. 77-79.
Reimann et al., Arch. Pharm. 1989, vol. 322, pp. 363-367.
Klapars, et al., J. Am. Chem. Soc. 2001, vol. 123, pp. 7727-7729.
Anderson, et al., Tetrahedron, 2002, vol. 58, pp. 8475-8481.
Touzeau et al., J. Med. Chem. 2003, vol. 46, pp. 1962-1979.
Altenbach et al., Synthesis and Structure-Activity Studies on N-[5-(1H-Imidazol-4-yl)-5,6,7,8-tetrahydro-1-naphthalenyl]methanesulfonamide, an Imidasole-Containing $\beta_{1A}$-Adrenoceptor Agonist, J. Med. Chem. (2004), 47: 3220-3235.
Amemiya et al., Synthesis and β-Adrenergic Activities of 2-and 4-Substituted Imidazoline and Imidazoline Analogues, J. Med. Chem. (1992), 35:750-755.
Bagley et al., Synthesis and $\beta_2$-Adrenegeric Activities of Imidazole and Imidazolidine Analogues: In Vitro and In Vivo Selectivity, Medicinal Chemistry Research (1994), 4:346-364.
Branchek et al., Trace amine receptors as targets for novel therapeutics: legend, myth and fact, Curr. Opin. Phamacol. (2003), 3:90-97.
Bunzow et al., Amphetamine, 3,4-Methylenedioxymethamphetamine, Lysergic Acid Diethylamide, and Metabolites of the catecholamine Neurotransmitters Are Agonists of a Rat Trace Amine Receptor, Molecular Pharmacology (2001), 60: 1181-1188.
Carroll et al., In Vitro and In Vivo Characterization of Alpha-1A Selective Agonists and Their Utility for Stress Incontinence, Med. Chem. Res. (2004), 13:134-148.
De Bernardis et al., Conformationally Defined Adregernic Agents. 5. Resolution, Absolute Configuration, and Pharmacological Characterization of the Enantiomers of 2-(5,6-Dihydroxy-1,2,3,4-tetrahydro-1-naphthyl)imidazoline: A Potent Agonist at β—Adrenoceptors, J. Med. Chem. (1987), 30:1011-1017.
Faust et al., Antihypertensive Agents: Derivatives of 2-Imidazoline and 1,4,5,6-Tetrahydropyrimidine, J. Org. Chem. (1961), 26: 4044-4047.
Hirashima et al., Three-Dimensional Common-Feature Hypotheses for Octopamine Agonist 2-(Arylimino)imidazolidines, Bioorganic & Medicinal Chemistry (2002), 10:117-123.
Holt, A., Imidazoline binding sites on receptors and enzymes:Emerging targets for novel antidepressant drugs?, Journal of Psychiatry & Neuroscience (2003), 28:409-414.
Jetter et al., Synthesis of 4-Substituted Imidazoles via Palladium-Catalyzed Cross-Coupling Reactions, Synthesis (1998), 829-831.
Law et al., Benzylimidazolines as $h5$-$HT_{1B/1D}$ Serotonin Receptor Ligands: A Structure-Affinity Investigation, J. Med. Chem. (1998), 41:2243-2251.
Lee et al., 4-[(N-Imidazol-2-ylmethyl)aniline]pyranopyridine Analogs as Novel Anti-Angiogenic Agents, Bull. Korean Chem. Soc. (2005), 25: 619-628.
Matsunaga et al., $C_{17,20}$ inhibitors. Part 2: Design, synthesis and structure-activity relationships of (2-naphthylmethyl)-1H-imidazoles as novel $C_{17,20}$-lyase inhibitors, Bioorganic & Medicinal Chemistry (2004), 4314.
McLennan, P;L., The Hypothermic Effect of Clonidine and Other Imidazolidines in Relation to their Ability to Enter the Central Nervous System in Mice, European Journal of Pharmacology (1981), 69:477-482.
Nathanson, J.A.,Phenyliminoimidazolines: Characterization of a Class of Potent Agonists of Octopamine-Sensitive Adenylate Cylcase and Their Use in Understanding the Pharmacology of Octopamine Receptors, Amer. Soc. Pharmacology (1985), 28:254-268.
Ojida et al., Sterocontrolled synthesis of (1S)-1-(1H-imidazol-4-yl)-1-(6-methoxy-2-napthyl)-2-methylpropan-1-ol as a potent $C_{17,20}$-lyase inhibitor,Tetrahedron: Asymmetry (2004), 15: 1555-1559.
Olmos et al., Imidazolines stimulate release of insulin from RIN-5AH cells independently from imidazoline $I_1$ and $I_2$ receptors, European Journal of Pharmacology (1994), 262: 41-48.
Prisinzano et al., 2-(aniline)imidazolines and 2-(benzyl)imidazoline derivatives as $h5$-$HT_{1D}$ serotonin receptor ligands, Bioorganic & Medicinal Chemistry Letter (2004), 14:4697-4699.
Savola et al., Cardiovascular and Sedative β-Adrenoceptor Effects of Detomidine-like Arylalkyl Imidazoles and Associated Derivatives, Drug Res. (1988), 38:29-35.

Timmermans et al., Characterization of β-Adrenoceptor Populations. Quantitive Relationships between Cardiovascular Effects Initiated at Central and Peripheral β-Adrenoceptors, J. Med. Chem. (1981), 24:502-507.

Timmermans et al., Correlations between Central Hypotensive and Peripheral Hypertensive Effects of Structurally Dissimilar Alpha-Adrenoceptor Agonists, Life Sciences (1981), 28:653-660.

Turner et al., A Facile Route to Imidazol-4-yl Anions and Their Reaction with Carbonyl Compounds, J. Org. Chem. (1991), 56: 5739-5740.

Lewis D.A. & Lieberman J.A., Neuron. vol. 28, pp. 325-334 (2000).

Vandenberg R. J. & Aubrey K. R., Exp. Opin. Ther. Targets vol. 5(4) pp. 507-518 (2001).

Nakazato A. & Okuyama S., Exp. Opin. Ther. Patents vol. 10(1) pp. 75-98 (2000).

Sharma T., Br. J. Psychiatry, vol. 174 (Suppl. 38) pp. 44-51 (1999).

Javitt D. C. et al., Biol. Psychiatry, vol. 45 pp. 668-679 (1999).

Mohn A. R. et al., Cell, vol. 98 pp. 427-436 (1999).

Bliss, T. V. & Collingridge G. L., Nature, vol. 361 pp. 31-39 (1993).

Tang J. P. et al., Nature, vol. 401, pp. 63-69 (1999).

Gainetdinov R. R. et al., Trends in Pharm. Sci. vol. 23(8) pp. 367-373 (2002).

Lopez-Corcuera B, et al., Mol. Mem. Biol. vol. 18 pp. 13-20 (2001).

Bergeron R. et al., Proc. Natl. Acad. Sci. USA vol. 95, pp. 15730-15734 (1998).

Chen et al., J. Neurophysiol. vol. 89(2) pp. 691-703 (2003).

Armer R. E. & Miller D. J., Exp. Opin. Ther. Patents vol. 11(4) pp. 563-572 (2001).

Pralong E. et al., Prog. in Neurobiol. vol. 67, pp. 173-202 (2002).

Carlsson M. L., J. Neural Trans. vol. 105, pp. 525-535 (1998).

Liebigs, Ann. Chem. 80: pp. 80-82 (1963) (English language translation attached).

Chem. Ber. vol. 97: 2276 (1964).

Chemical Abstract XP002435251.

Chemical Abstract XP002435252.

Chemical Abstract XP002436293.

Cordi, A. et al, *Jour. of Med. Chem.*, 44:5 (2001) 787-805 XP002498467.

Amemiya, Y. et al, *Synthetic Communications*, 20:16 (1990) 2483-2489 XP009084142.

Wainscott, D.B. et al, *Jour. of Pharmacology and Experimental Therapeutics*, 320:1 (2007) 475-485 XP002473115.

\* cited by examiner

4-IMIDAZOLINES

PRIORITY TO RELATED APPLICATION(S)

This application claims the benefit of European Patent Application No. 07111623.0, filed Jul. 3, 2007, which is hereby incorporated by reference in its entirety.

BACKGROUND OF INVENTION

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9]. For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "cross reacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gas. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

REFERENCES USED

1 Deutch, A. Y. and Roth, R. H. (1999) Neurotransmitters. In *Fundamental Neuroscience* (2$^{nd}$ edn) (Zigmond, M. J., Bloom, F. E., Landis, S. C., Roberts, J. L, and Squire, L. R., eds.), pp. 193-234, Academic Press;
2 Wong, M. L. and Licinio, J. (2001) Research and treatment approaches to depression. *Nat. Rev. Neurosci.* 2, 343-351;
3 Carlsson, A. et al. (2001) Interactions between monoamines, glutamate, and GABA in schizophrenia: new evidence. *Annu. Rev. Pharmacol. Toxicol.* 41, 237-260;
4 Tuite, P. and Riss, J. (2003) Recent developments in the pharmacological treatment of Parkinson's disease. *Expert Opin. Investig. Drugs* 12, 1335-1352,
5 Castellanos, F. X. and Tannock, R. (2002) Neuroscience of attention-deficit/hyperactivity disorder: the search for endophenotypes. *Nat. Rev. Neurosci.* 3, 617-628;
6 Usdin, Earl; Sandler, Merton; Editors. *Psychopharmacology Series, Vol. 1: Trace Amines the Brain. [Proceedings of a Study Group at the 14th Annual Meeting of the American College of Neuropsychopharmacology*, San Juan, Puerto Rico] (1976);
7 Lindemann, L. and Hoener, M. (2005) A renaissance in trace amines inspired by a novel GPCR family. *Trends in Pharmacol. Sci.* 26, 274-281;
8 Branchek, T. A. and Blackburn, T. P. (2003) Trace amine receptors as targets for novel therapeutics: legend, myth and fact. *Curr. Opin. Pharmacol.* 3, 90-97;
9 Premont, R. T. et al. (2001) Following the trace of elusive amines. *Proc. Natl. Acad. Sci. U.S.A.* 98, 9474-9475;
10 Mousseau, D. D. and Butterworth, R. F. (1995) A high-affinity [3H] tryptamine binding site in human brain. *Prog. Brain Res.* 106, 285-291;
11 McCormack, J. K. et al. (1986) Autoradiographic localization of tryptamine binding sites in the rat and dog central nervous system. *J. Neurosci.* 6, 94-101;
12 Dyck, L. E. (1989) Release of some endogenous trace amines from rat striatal slices in the presence and absence of a monoamine oxidase inhibitor. *Life Sci.* 44, 1149-1156;
13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;
14 Lindemann, L. et al. (2005) Trace amine associated receptors form structurally and functionally distinct subfamilies of novel G protein-coupled receptors. *Genomics* 85, 372-385.

SUMMARY OF THE INVENTION

The present invention provides compounds of formula

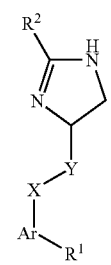

wherein $R^1$ is hydrogen, halogen or lower alkyl;

$R^2$ is hydrogen or amino;

X—Y is —(CH$_2$)$_n$—, N(R)—CH$_2$—, —O—CH$_2$— or —S—CH$_2$—;

Ar is phenyl or naphthyl;

n is 1 or 2;

R is hydrogen or lower alkyl;

and their pharmaceutically active salts, with the exclusion of the racemic compound 4-benzyl-4,5-dihydro-1H-imidazole or its tautomer (CAS 131548-83-9).

The specific compound excluded from the scope of new compounds of formula I is described for example in the below mentioned references or is enclosed in public chemical libraries.

The invention includes all racemic mixtures, all their corresponding enantiomers and/or optical isomers. In addition, all tautomeric forms of compounds of formula I are also encompassed by the present invention.

The invention also provides pharmaceutical compositions containing a therapeutically effective amount of a compound of formula I or a pharmaceutically active salt thereof and a pharmaceutically acceptable carrier. The invention also provides methods for the preparation of compounds and compositions of the invention.

Compounds of formula I have a good affinity to the trace amine associated receptors (TAARs), especially for TAAR1.

The compounds are useful for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety and attention deficit hyperactivity disorder (ADHD).

DETAILED DESCRIPTION OF THE INVENTION

The following definitions of general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "halogen" denotes chlorine, iodine, fluorine and bromine.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

Preferred compounds of formula I are those wherein Ar is naphthyl.

Further preferred compounds of formula I are those, wherein Ar is naphthyl and X—Y is —CH$_2$—, for example the following compounds rac-4-naphthalen-1-ylmethyl-4,5-dihydro-1H-imidazole or tautomer or (RS)-4-(8-ethyl-naphthalen-1-ylmethyl)-4,5-dihydro-1H-imidazole or tautomer.

Preferred compounds of formula I are those wherein Ar is phenyl.

Further preferred compounds of formula I are those, wherein Ar is phenyl and X—Y is —CH$_2$—CH$_2$—, for example the following compounds rac-4-phenethyl-4,5-dihydro-1H-imidazole or tautomer or rac-4-[2-(4-chloro-phenyl)-ethyl]-4,5-dihydro-1H-imidazole or tautomer.

Further preferred compounds of formula I are those, wherein Ar is phenyl and X—Y is —N(R)—CH$_2$—, for example the following compounds rac-(4,5-dihydro-3H-imidazol-4-ylmethyl)-ethyl-phenyl-amine or tautomer or (4,5-dihydro-3H-imidazol-4-ylmethyl)-methyl-phenyl-amine or tautomer.

Preferred compounds of formula I are those wherein X—Y is —O—CH$_2$—.

Preferred compounds of formula I are those wherein X—Y is —S—CH$_2$—.

The present compounds of formula I and their pharmaceutically acceptable salts can be prepared by methods known in the art, for example, by processes described below, which process comprises a) reacting a di-amino compound of formula

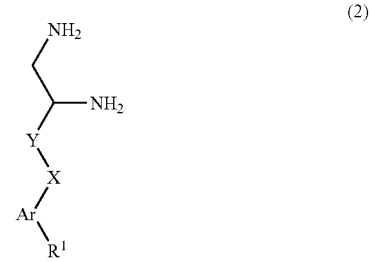

with a formamidinium salt of formula

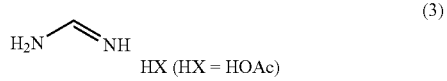

to give a mixture of tautomeric compounds of formulas

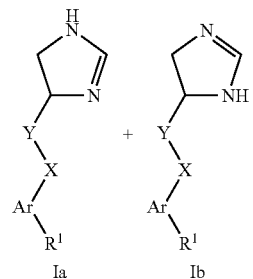

wherein the substituents are as defined above, or b) reacting a compound of formula

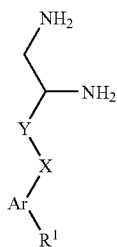
(2)

with BrCN (4)

to give a compound of formula

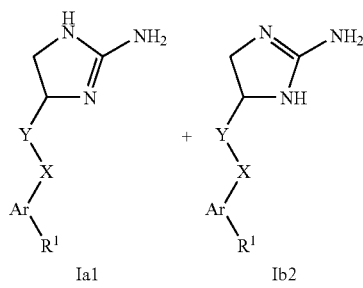

and, if desired, converting the compounds obtained into pharmaceutically acceptable acid addition salts.

The compounds of formula I can be prepared in accordance with the process variants as described above and with the following schemes 1 and 2. The starting materials are either commercially available, are otherwise known in the chemical literature, or can be prepared in accordance with methods well known in the art.

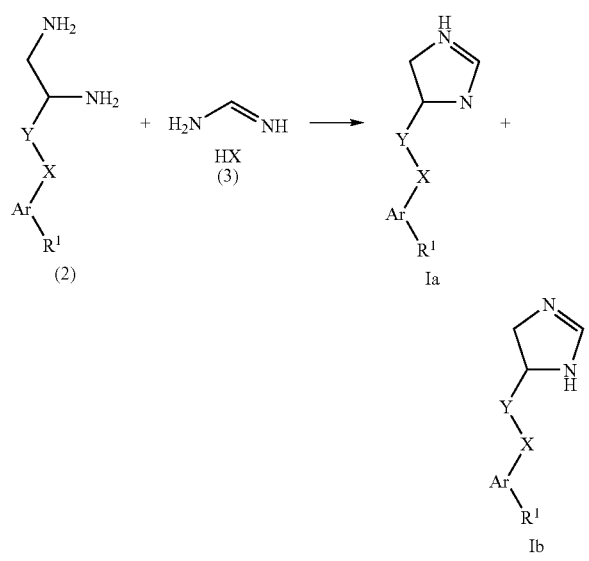

A 1,2-diamino compound of formula (2) is reacted with a formamidinium salt of formula (3), such as formamidinium acetate (in this case HX=HOAc), at room temperature or elevated temperature in an inert solvent (preferred methanol or ethanol) to form compounds I as a mixture of tautmers Ia and Ib. Both tautomeric forms are objects of the present invention.

The procedure is described for instance in:

[1] J. Med. Chem. 2004, 47, 3220

Instead of the formamidinium salt (3) also other reagents are described to transform a 1,2-diamino compound (2) into an imidazoline compounds I:

[2] ethyl formiate: Synthetic Communications, 2004, 34, 3535

[3] triethylorthoformiate: Tetrahedron Lett. 2003, 44, 9111

[4] dimethylformamid dimethylacetal: J. Org. Chem. 1997, 62, 3586

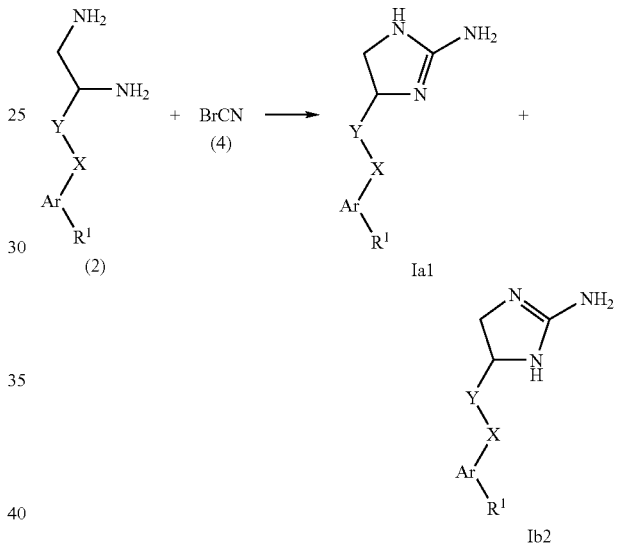

To synthesize 2-amino-imidazoline compounds of formula Ia1 and Ib2 a 1,2-diamino compound of formula (2) is reacted with cyanogen bromide (4) at room temperature or elevated temperature in a solvent such as tetrahydrofurane. A base such as potassium carbonate might be added. Both tautomeric forms Ia1 and Ib2 are objects of the present invention.

The procedure is mentioned for instance in:

[5] J. Amer. Chem. Soc. 1964, 86, 2241

The 1,2-diamino compounds (2) used as starting materials in scheme 1 and 2 are available using known methods such as reduction of 2-aminonitriles or 1,2-diazido compounds. Such methods are described for instance in:

[6] J. Med. Chem. 1985, 28, 1280

[7] Helv. Chim. Acta 2005, 88, 1486

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically acceptable addition salts possess valuable pharmacological properties. Specifically, compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM $Mg^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # C.RL-1573) were cultured essentially as described Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Membrane Preparation and Radioligand Binding

Cells at confluence were rinsed with ice-cold phosphate buffered saline without $Ca^{2+}$ and $Mg^{2+}$ containing 10 mM EDTA and pelleted by centrifugation at 1000 rpm for 5 min at 4° C. The pellet was then washed twice with ice-cold phosphate buffered saline and cell pellet was frozen immediately by immersion in liquid nitrogen and stored until use at −80° C. Cell pellet was then suspended in 20 ml HEPES-NaOH (20 mM), pH 7.4 containing 10 mM EDTA, and homogenized with a Polytron (PT 3000, Kinematica) at 10,000 rpm for 10 s. The homogenate was centrifuged at 48,000×g for 30 min at 4° C. and the pellet resuspended in 20 ml HEPES-NaOH (20 mM), pH 7.4 containing 0.1 mM EDTA (buffer A), and homogenized with a Polytron at 10,000 rpm for 10 s. The homogenate was then centrifuged at 48,000×g for 30 min at 4° C. and the pellet resuspended in 20 ml buffer A, and homogenized with a Polytron at 10,000 rpm for 10 s. Protein concentration was determined by the method of Pierce (Rockford, Ill.). The homogenate was then centrifuged at 48,000×g for 10 min at 4° C., resuspended in HEPES-NaOH (20 mM), pH 7.0 including $MgCl_2$ (10 mM) and $CaCl_2$ g protein per ml and (2 mM) (buffer B) at 200 homogenized with a Polytron at 10,000 rpm for 10 s.

Binding assay was performed at 4° C. in a final volume of 1 ml, and with an incubation time of 30 min. The radioligand [$^3$H]-rac-2-(1,2,3,4-tetrahydro-1-naphthyl)-2-imidazoline was used at a concentration equal to the calculated $K_d$ value of 60 nM to give a bound at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 µM). Competing ligands were tested in a wide range of concentrations (10 µM-30 µM). The final dimethylsulphoxide concentration in the assay was 2%, and it did not affect radioligand binding. Each experiment was performed in duplicate. All incubations were terminated by rapid filtration through UniFilter-96 plates (Packard Instrument Company) and glass filter GF/C, pre-soaked for at least 2 h in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 µl/well, Packard Instrument Company) and bound radioactivity was counted by a TopCount Microplate Scintillation Counter (Packard Instrument Company).

The preferred compounds show a Ki value (µM) in mouse on TAAR1 in the range of 0.005 to 0.5. Representative compounds are shown in the table below.

| Example | Ki (µM) mouse |
| --- | --- |
| 2 | 0.005 |
| 3 | 0.060 |
| 4 | 0.253 |
| 6 | 0.078 |
| 7 | 0.182 |
| 10 | 0.327 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragees, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. gelatin Lactose, corn starch or derivatives thereof, talc, stearic acids or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragees, hard and soft gelatin capsules, solutions, emulsions, or suspensions. The pharmaceutical compositions also can be administered rectally, for example, in the form of suppositories, or parenterally, for example, in the form of injectable solutions.

The most preferred indications in accordance with the present invention are those, which include disorders of the central nervous system, for example the treatment or prevention of schizophrenia, depression, cognitive impairment and Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXPERIMENTAL

The following examples illustrate the invention but are not intended to limit its scope.

Example 1

(R)-4-Benzyl-4,5-dihydro-1H-imidazole or tautomer

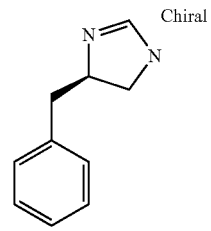

To a solution of (2R)-3-phenyl-1,2-propanediamine (0.20 g, 1.33 mmol) in ethanol (5 ml) was added formamidine acetate (0.15 g, 1.45 mmol) and the mixture was stirred overnight at room temperature. The solvent was evaporated, sodium hydroxide (2N, 5 ml) was added and the mixture was extracted 3 times with dichloromethane (10 ml). The combined organic layers were dried over magnesium sulfate and evaporated. The residue was purified by chromatography (column: Isolute® Flash-NH₂ from Separtis; eluent:ethyl acetate/methanol=90:10) to yield a colorless oil (0.20 g, 92%); MS (ISP): 161.4 ((M+H)⁺).

Example 2 rac-4-Naphthalen-1-ylmethyl-4,5-dihydro-1H-imidazole or tautomer

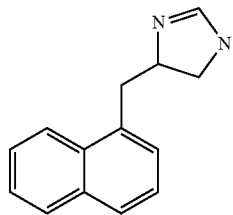

The title compound, MS (ISP): 211.1 ((M+H)⁺) was obtained in comparable yield analogous to the procedure described for Example 1 using 3-(1-naphthalenyl)-1,2-propanediamine instead of (2R)-3-phenyl-1,2-propanediamine.

Example 3 rac-4-Phenethyl-4,5-dihydro-1H-imidazole or tautomer

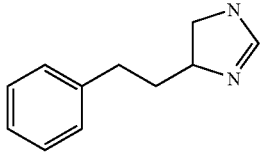

The title compound, MS (ISP): 175.0 ((M+H)⁺) was obtained in comparable yield analogous to the procedure described for Example 1 using 4-phenyl-1,2-butanediamine instead of (2R)-3-phenyl-1,2-propanediamine.

Example 4 rac-(4,5-Dihydro-3H-imidazol-4-ylmethyl)-ethyl-phenyl-amine or tautomer

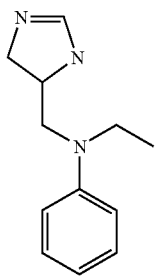

a) rac-3-(Ethyl-phenyl-amino)-propane-1,2-diol

A mixture of N-ethylaniline (1.21 g, 10 mmol), glycidol (1.11 g, 15 mmol) and ethanol (1 ml) was heated by microwave irradiation for 10 min at 120° C. The mixture was dissolved in water (10 ml) and extracted with ethyl acetate (3 times 25 ml). The combined organic layers were dried over magnesium sulfate and evaporated. The residue was purified by chromatography (SiO₂, ethyl acetate/heptane=1:2) to yield a colorless liquid (1.85 g, 94%); MS (ISP): 196.3 ((M+H)⁺).

b) rac-(2,3-Diazido-propyl)-ethyl-phenyl-amine

A solution of rac-3-(ethyl-phenyl-amino)-propane-1,2-diol (1.80 g, 9.2 mmol) and triethylamine (2.05 g, 20.3 mmol) in dichloromethane (10 ml) was added slowly to an ice cooled solution of methane sulfonyl chloride (2.2 g, 19.35 mmol) in dichloromethane (20 ml). The reaction mixture was kept in a refrigerator overnight. For workup it was washed with hydrochloric acid (0.1M, 20 ml), sodium bicarbonate solution (20 ml) and water (20 ml). The organic layer was dried over magnesium sulfate and evaporated. The residue was dissolved in dimethylformamide (35 ml), sodium azide (3.9 g, 60 mmol) was added and the mixture was stirred overnight at 60° C. After cooling, water (70 ml) and ethyl acetate (100 ml) were added. The organic layer was separated and the mixture was extracted again with ethyl acetate. The combined organic layers were washed with brine, dried over magnesium sulfate and evaporated. The residue was purified by chromatography (SiO₂, ethyl acetate/heptane=1:4) to yield a light yellow liquid (1.17 g, 52%).

c) rac-N1-Ethyl-N1-phenyl-propane-1,2,3-triamine

To a solution of rac-(2,3-diazido-propyl)-ethyl-phenyl-amine (0.245 g, 1 mmol) in methanol (5 ml) was added platinum(IV)-oxide (50 mg) and the mixture was hydrogenated at atmospheric pressure overnight. The catalyst was removed by filtration over celite and the filtrate was evaporated. The residue was purified by chromatography (column: Isolute® Flash-NH₂ from Separtis; eluent: ethyl acetate) to yield a light yellow liquid (0.19 g, 98%); MS (ISP): 194.1 ((M+H)⁺).

d) rac-(4,5-Dihydro-3H-imidazol-4-ylmethyl)-ethyl-phenyl-amine or tautomer

To a solution of rac-N1-ethyl-N1-phenyl-propane-1,2,3-triamine (0.19 g, 1.0 mmol) in ethanol (5 ml) was added formamidine acetate (0.11 g, 1.08 mmol) and the mixture was stirred overnight at room temperature. The solvent was evaporated, water (5 ml) was added and the mixture was extracted 3 times with dichloromethane (10 ml). The combined organic layers were dried over magnesium sulfate and evaporated. The residue was purified by chromatography (column: Isolute® Flash-NH₂ from Separtis; eluent:ethyl acetate/methanol=90:10) to yield an off-white amorphous solid (0.042 g, 21%); MS (ISP): 204.1 ((M+H)⁺).

Example 5

(S)-4-Benzyl-4,5-dihydro-1H-imidazole or tautomer

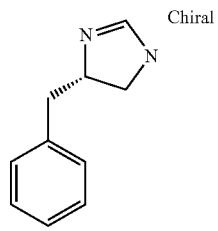

The title compound, MS (ISP): 161.4 (M+H)⁺ was obtained in comparable yield analogous to the procedure described for Example 1 using (2S)-3-phenyl-1,2-propanediamine instead of (2R)-3-phenyl-1,2-propanediamine.

Example 6

(RS)-4-(8-Ethyl-naphthalen-1-ylmethyl)-4,5-dihydro-1H-imidazole or tautomer a) 8-Bromo-naphthalene-1-carboxylic acid ethyl ester

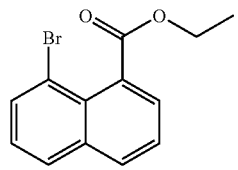

A solution of 8-bromo-naphthalene-1-carboxylic acid (1.6 g) in DMF (15 ml) was treated with potassium carbonate (2.2 g) and iodoethane (1.03 ml). The reaction mixture was stirred overnight at r.t., then quenched with water and extracted with ethyl acetate. The organics were dried over MgSO₄, filtered and concentrated. The crude product was purified by column chromatography (silica gel; gradient: cyclohexane→cyclohexane/EtOAc 1:1) to give 8-bromo-naphthalene-1-carboxylic acid ethyl ester (1.57 g) as colorless liquid. MS (ISP): 279.1 ((M+H)⁺).

b) 8-Vinyl-naphthalene-1-carboxylic acid ethyl ester

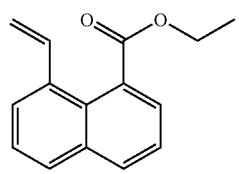

A stream of argon was passed through a solution of 8-bromo-naphthalene-1-carboxylic acid ethyl ester (1.44 g) in toluene (15 ml) for 15 min. Then tetrakis(triphenylphosphine)palladium (179 mg) and vinyltributylstannane (1.65 ml) were added. The reaction mixture was heated under an Argon atmosphere to 100° C. overnight, then cooled to r.t. and treated with 4M potassium fluoride solution. The suspension was stirred for 10 min and then filtered. The solids were washed with toluene. The filtrate was washed with 4M KF solution, then dried over MgSO₄, filtered and concentrated. The crude product was purified by column chromatography (silica gel; gradient:cyclohexane→cyclohexane/EtOAc 3:2) to give 8-vinyl-naphthalene-1-carboxylic acid ethyl ester (1.11 g) as light yellow liquid. MS (ISP): 227.1 ((M+H)⁺).

c) 8-Ethyl-naphthalene-1-carboxylic acid ethyl ester

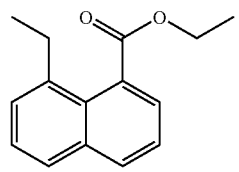

A solution of 8-vinyl-naphthalene-1-carboxylic acid ethyl ester (1.1 g) in EtOH (25 ml) was treated with acetic acid (1 ml) and Pd/C (270 mg; 10%) and hydrogenated at normal pressure overnight. The catalyst was filtered off. The filtrate was concentrated. The crude product was isolated by chromatography (silica gel; gradient:cyclohexane→cyclohexane/EtOAc 3:2) to give 8-ethyl-naphthalene-1-carboxylic acid ethyl ester (1.05 g) as colorless liquid. MS (ISP): 229.3 ((M+H)⁺).

d) (8-Ethyl-naphthalen-1-yl)-methanol

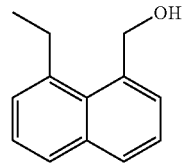

A solution of 8-ethyl-naphthalene-1-carboxylic acid ethyl ester (1.04 g) in THF (30 ml) was cooled to 0° C. and treated with diisobutyl aluminium hydride solution (11.4 ml; 1.2 M in toluene). The reaction mixture was stirred for 2 hrs at r.t., then again cooled to 0° C. and treated with H₂O (50 ml) and 0.1N HCl (50 ml). The mixture was extracted with EtOAc. The organics were dried over MgSO₄, filtered and concentrated. The crude product was purified by column chromatography (silica gel; gradient cyclohexane→cyclohexane/EtOAc 4:1) to give (8-ethyl-naphthalen-1-yl)-methanol (769 mg) as white solid. MS (ISP): 187.3 ((M+H)⁺).

e) 1-Bromomethyl-8-ethyl-naphthalene

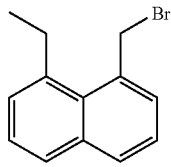

A solution of (8-ethyl-naphthalen-1-yl)-methanol (760 mg) in dichloromethane (15 ml) was cooled to 0° C. and treated with carbon tetrabromide (2.03 g). A solution of triphenylphosphine (1.28 g) in dichloromethane (15 ml) was added dropwise. The reaction mixture was stirred at r.t. overnight, then concentrated. The crude product was purified by column chromatography (silica gel; cyclohexane→cyclohexane/EtOAc 4:1) to give 1-bromomethyl-8-ethyl-naphthalene (670 mg) as light yellow liquid.

f) (RS)-2-Amino-3-(8-ethyl-naphthalen-1-yl)-propionitrile

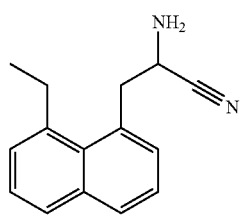

A suspension of N-(diphenylmethylene)aminoacetonitrile (449 mg) in dichloromethane (7 ml) was cooled to 0° C. and treated under an argon atmosphere with tetrabutylammonium bromide (61 mg) and KOH (111 mg). A solution of 1-bromo-methyl-8-ethyl-naphthalene (470 mg) in dichloromethane (8 ml) was added dropwise. The reaction mixture was stirred at r.t. overnight, then filtered. The solid was washed with dichloromethane. The filtrated was concentrated. The residue was taken up in diethyl ether (16 ml) and water (16 ml) and stirred overnight. The layers were separated. The aqueous layer was brought to pH 12 with 4N NaOH solution and extracted with $CH_2Cl_2$/MeOH 95:5. The organic layer was dried over $MgSO_4$, filtered and concentrated. The crude product was purified by column chromatography (silica gel; eluent: $CH_2Cl_2 \rightarrow CH_2Cl_2$/MeOH 95:5) to give (RS)-2-amino-3-(8-ethyl-naphthalen-1-yl)-propionitrile (243 mg) as light brown oil. MS (ISP): 225.4 ((M+H)$^+$).

g) (RS)-3-(8-Ethyl-naphthalen-1-yl)-propane-1,2-diamine

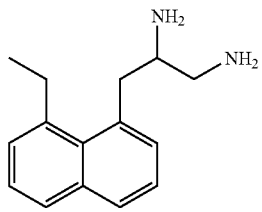

A suspension of $LiAlH_4$ (117 mg) in THF (2 ml) was cooled to 0° C. and treated under an argon atmosphere with a solution of (RS)-2-amino-3-(8-ethyl-naphthalen-1-yl)-propionitrile (230 mg) in THF (4 ml). The reaction mixture was stirred for 5 hrs at r.t., then treated sequentially at 0° C. with 0.1 ml $H_2O$, 0.1 ml 4N NaOH and 0.5 ml $H_2O$. After stirring for 30 min, the solid was filtered off and washed with THF. The filtrate was concentrated. The crude product was isolated by column chromatography (silica gel; eluent: $CH_2Cl_2 \rightarrow CH_2Cl_2$/MeOH 9:1) to give 3-(8-ethyl-naphthalen-1-yl)-propane-1,2-diamine (66 mg) as light brown oil. MS (ISP): 229.3 ((M+H)$^+$).

h) (RS)-4-(8-Ethyl-naphthalen-1-ylmethyl)-4,5-dihydro-1H-imidazole or tautomer

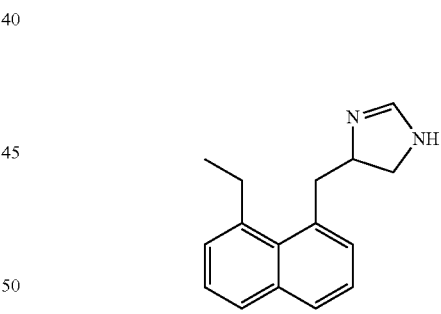

A solution of 3-(8-ethyl-naphthalen-1-yl)-propane-1,2-diamine (60 mg) in EtOH (6 ml) was treated at r.t. under an argon atmosphere with formamidine acetate (30 mg). The reaction mixture was stirred at r.t. overnight, then concentrated. The crude product was purified by column chromatography (silica gel; eluent: $CH_2Cl_2 \rightarrow CH_2Cl_2$/MeOH 9:1) to give (RS)-4-(8-ethyl-naphthalen-1-ylmethyl)-4,5-dihydro-1H-imidazole (38 mg) as light yellow gum. MS (ISP): 239.3 ((M+H)$^+$).

Example 7

(4,5-Dihydro-3H-imidazol-4-ylmethyl)-methyl-phenyl-amine or tautomer

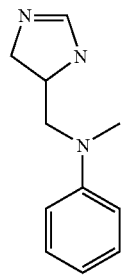

The title compound, MS (ISP): 190.2 (M+H)$^+$ was obtained in comparable yield analogous to the procedure described for Example 4 using N-methylaniline instead of N-ethylaniline in step a).

Example 8

4-{[(3-Chloro-phenyl)-methyl-amino]-methyl}-4,5-dihydro-1H-imidazol-2-ylamine or tautomer

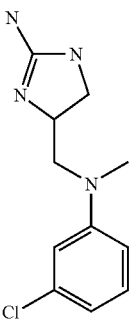

a) N1-(3-Chloro-phenyl)-N1-methyl-propane-1,2,3-triamine

N1-(3-Chloro-phenyl)-N1-methyl-propane-1,2,3-triamine, MS (ISP): 214.2 (M+H)$^+$ was prepared according to the procedure described for Example 4, steps a), b) and c) starting with 3-chloro-N-methylaniline instead of N-ethylaniline.

b) 4-{[(3-Chloro-phenyl)-methyl-amino]-methyl}-4,5-dihydro-1H-imidazol-2-ylamine N1-(3-Chloro-phenyl)-N1-methyl-propane-1,2,3-triamine (0.321 g, 1.5 mmol) was dissolved in tetrahydrofurane (5 ml) and potassium carbonate (0.249 g, 1.8 mmol) was added. Under cooling with an ice-bath a solution of cyanogen bromide (0.191 g, 1.8 mmol) in tetrahydrofurane (5 ml) was added dropwise. The cooling bath was removed and stirring was continued for one hour. Ethyl acetate (50 ml) and water (20 ml) were added and the organic layer was separated. The mixture was extracted again with ethyl acetate. The combined organic layers were dried over magnesium sulfate and evaporated. The residue was recrystallised from ethyl acetate to yield 0.1 g (28%) of a white solid; MS (ISP): 239.2 ((M+H)$^+$).

Example 9

4-(4-Chloro-benzyl)-4,5-dihydro-1H-imidazole or tautomer

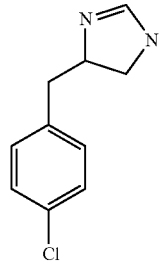

The title compound, MS (ISP): 195.1 (M+H)$^+$ was obtained in comparable yield analogous to the procedure described for Example 1 using 3-(4-chlorophenyl)-1,2-propanediamine instead of (2R)-3-phenyl-1,2-propanediamine.

Example 10 rac-4-[2-(4-Chloro-phenyl)-ethyl]-4,5-dihydro-1H-imidazole or tautomer

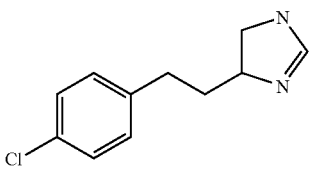

a) 2-Amino-4-(4-chloro-phenyl)-butyronitril

To 3-(4-chlorophenyl)-propionaldehyde (0.74 g, 4.39 mmol) was added zinc iodide (0.07 g, 0.22 mmol) and trimethylsilyl cyanide (0.522 g, 5.27 mmol) with caution (exothermic reaction). After stirring the mixture at room temperature for 20 min a solution of ammonia in methanol (7N, 4.4 ml, 31 mmol) was added and stirring was continued overnight. The solvent was evaporated and the residue was purified by chromatography (column: Isolute® Flash-NH$_2$ from Separtis; eluent:heptane/ethyl acetate=2:1) to yield a light yellow liquid (0.43 g, 50%); MS (ISP): 195.3 ((M+H)$^+$).

b) 4-(4-Chlorophenyl)-1,2-butanediamine

A solution of 2-amino-4-(4-chloro-phenyl)-butyronitril (0.425 g, 2.18 mmol) in tetrahydrofurane (4 ml) was added dropwise to a suspension of lithium aluminum hydride (0.331 g, 8.73 mmol) in tetrahydrofurane (4 ml) at 0° C. under argon atmosphere. The reaction mixture was allowed to reflux overnight. After cooling to 0° C. solid sodium sulphate decahydrate was added and stirring was continued for 1 hour. The grey suspension was filtered through Celite and the solvent was evaporated. The residue was purified by chromatography (column: Isolute® Flash-NH$_2$ from Separtis; eluent:ethyl acetate/methanol=90:10) to yield a colorless oil (0.091 g, 21%); MS (ISP): 199.1 ((M+H)⁺).

c) rac-4-[2-(4-Chloro-phenyl)-ethyl]-4,5-dihydro-1H-imidazole or tautomer

To a solution of 4-(4-chlorophenyl)-1,2-butanediamine (0.084 mg, 0.42 mmol) in ethanol (8 ml) was added formamidine acetate (0.15 g, 1.45 mmol) and the mixture was stirred overnight at room temperature. The solvent was evaporated, water (5 ml) was added and the mixture was extracted 3 times with dichloromethane (10 ml). The combined organic layers were dried over magnesium sulfate and evaporated. The residue was purified by chromatography (column: Isolute® Flash-NH₂ from Separtis; eluent:ethyl acetate/methanol=90:10) to yield an off-white amorphous solid (0.041 g, 47%); MS (ISP): 209.3 ((M+H)⁺).

Example 11 rac-5-(4-Chloro-phenoxymethyl]-4,5-dihydro-1H-imidazole or tautomer

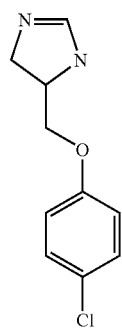

a) rac-1-Azido-3-(4-chloro-phenoxy)-propane

A solution of sodium azide (0.977 g, 15 mmol) in water (1 ml) was added to a solution of rac-(4-chlorophenoxy)oxirane (1.85 g, 10 mmol) in acetonitrile (11 ml). The mixture was heated to reflux for overnight. Saturated ammonium chloride solution (20 ml) was added and the mixture was extracted with ethyl acetate (3 times 25 ml). The combined organic layers were dried over magnesium sulfate and evaporated. The residue was purified by chromatography (SiO₂, ethyl acetate/heptane=1:1) to yield a colorless liquid (1.73 g, 76%); MS (EI): 227.1 ((M⁺).

b) rac-1-Chloro-4-(2,3-diazido-propoxy)-benzene

A solution of p-toluenesulfonyl chloride (1.88 g, 10 mmol) in pyridine (9 ml) was added dropwise within 1 hour to a solution of rac-1-azido-3-(4-chloro-phenoxy)-propane (1.73 g, 8 mmol) in pyridine (9 ml) at a temperature between −5° C. and −2° C. The reaction mixture was kept for 48 hours at 4° C., and then poured into ice-water. The mixture was extracted with ethyl acetate (3 times 25 ml). The combined organic layers were dried over magnesium sulfate and evaporated. The residue was purified by chromatography (SiO₂, ethyl acetate/heptane=1:1) to yield a colorless oil (1.87 g, 64%). This compound was dissolved in dimethylformamide (6 ml), and sodium azide (0.80 g, 12 mmol) was added. The mixture was stirred for 4 hours at 90° C. For work-up water (20 ml) and ethyl acetate (50 ml) is added to the mixture. The layers are separated and the aqueous layer is extracted again with ethyl acetate. The combined organic layers were dried over magnesium sulfate and evaporated. The residue was purified by chromatography (SiO₂, ethyl acetate/heptane=1:1) to yield a colorless liquid (0.89 g, 72%); MS (EI): 252.1; 254.1 ((M⁺).

c) rac-3-(4-Chloro-phenoxy)-propane-1,2-diamine

To a solution of rac-1-chloro-4-(2,3-diazido-propoxy)-benzene (0.89 g, 3.5 mmol) in methanol (5 ml) was added palladium on charcoal (50 mg) and the mixture was hydrogenated at atmospheric pressure for 1 hour. The catalyst was removed by filtration over celite and the filtrate was evaporated. The residue was purified by chromatography (column: Isolute® Flash-NH₂ from Separtis; eluent: ethyl acetate) to yield a light yellow liquid (0.19 g, 27%); MS (ISP): 201.3 ((M+H)⁺).

rac-4-(4-Chloro-phenoxymethyl]-4,5-dihydro-1H-imidazole

To a solution of 3-(4-chloro-phenoxy)-propane-1,2-diamine (0.19 g, 0.95 mmol) in ethanol (5 ml) was added formamidine acetate (0.1 g, 1.0 mmol) and the mixture was stirred overnight at room temperature. The solvent was evaporated, water (5 ml) was added and the mixture was extracted 3 times with dichloromethane (10 ml). The combined organic layers were dried over magnesium sulfate and evaporated. The residue was purified by chromatography (column: Isolute® Flash-NH₂ from Separtis; eluent:ethyl acetate/methanol=90:10) to yield a light yellow oil (0.063 g, 32%); MS (ISP): 211.2 ((M+H)⁺).

Example 12

(R)-5-Phenylsulfanylmethyl-4,5-dihydro-1H-imidazole or tautomer

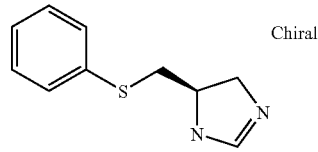

The title compound, MS (ISP): 193.1 (M+H)⁺) was obtained in comparable yield analogous to the procedure described for Example 1 using (2R)-3-(phenylthio)-1,2-propanediamine instead of (2R)-3-phenyl-1,2-propanediamine.

Example 13

(R)-5-Phenylsulfanylmethyl-4,5-dihydro-1H-imidazol-2-ylamine hydrobromide or tautomer

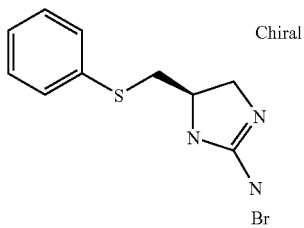

(2R)-3-(Phenylthio)-1,2-propanediamine (0.20 g, 1.1 mmol) was dissolved in toluene (3 ml) and a solution of cyanogen bromide (0.116 g, 1.1 mmol) in toluene (1 ml) was added dropwise at room temperature. The mixture is allowed to stir for 90 min. After evaporation of the solvent the residue was dissolved in ethanol (1.5 ml). By slowly adding ethyl acetate (8 ml) a light brown solid precipitated, 0.152 g (66%), MS (ISP): 207.9 (M+H)$^+$).

The invention claimed is:

1. A compound of formula I

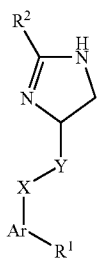

I wherein
R$^1$ is hydrogen, halogen or lower alkyl;
R$^2$ is hydrogen;
X—Y is —(CH$_2$)$_n$—, N(R)—CH$_2$—, or —S—CH$_2$—;
Ar is phenyl or naphthyl;
n is 1 or 2;
R is hydrogen or lower alkyl;
or a pharmaceutically active salt thereof, with the exclusion of the racemic compound 4-benzyl-4,5-dihydro-1H-imidazole or its tautomer.

2. The compound of claim 1, wherein Ar is naphthyl.

3. The compound of claim 2, wherein X—Y is —CH$_2$—.

4. The compound of claim 3, selected from the group consisting of rac-4-naphthalen-1-ylmethyl-4,5-dihydro-1H-imidazole or tautomer and (RS)-4-(8-ethyl-naphthalen-1-ylmethyl)-4,5-dihydro-1H-imidazole or tautomer.

5. The compound of claim 1, wherein Ar is phenyl.

6. The compound of claim 5, wherein X—Y is —CH$_2$—CH$_2$—.

7. The compound of claim 6, selected from the group consisting of rac-4-phenethyl-4,5-dihydro-1H-imidazole or tautomer and rac-4-[2-(4-chloro-phenyl)-ethyl]-4,5-dihydro-1H-imidazole or tautomer.

8. The compound of claim 5, wherein X—Y is —N(R)—CH$_2$—.

9. The compound of claim 8, selected from the group consisting of rac-(4,5-dihydro-3H-imidazol-4-ylmethyl)-ethyl-phenyl-amine or tautomer and (4,5-dihydro-3H-imidazol-4-ylmethyl)-methyl-phenyl-amine or tautomer.

10. The compound of claim 1, wherein X—Y is —S—CH$_2$—.

11. A pharmaceutical composition comprising a therapeutically effective amount of a compound of formula I

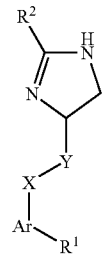

I wherein
R$^1$ is hydrogen, halogen or lower alkyl;
R$^2$ is hydrogen;
X—Y is —(CH$_2$)$_n$—, N(R)—CH$_2$—, or —S—CH$_2$—;
Ar is phenyl or naphthyl;
n is 1 or 2;
R is hydrogen or lower alkyl;
or a pharmaceutically active salt thereof, with the exclusion of the racemic compound 4-benzyl-4,5-dihydro-1H-imidazole or its tautomer
and a pharmaceutically acceptable carrier.

* * * * *